(12) United States Patent  
Takamatsu et al.

(10) Patent No.: US 7,889,837 B2
(45) Date of Patent: Feb. 15, 2011

(54) X-RAY COMPUTED TOMOGRAPHIC APPARATUS

(75) Inventors: Tomonao Takamatsu, Tokyo (JP); Hitoshi Hattori, Yokohama (JP); Hideo Iwasaki, Kawasaki (JP); Harunobu Fukushima, Tokyo (JP); Rika Hosaka, Yokohama (JP); Tomohiko Jimbo, Fujisawa (JP); Tetsuya Sadotomo, Otawara (JP); Tomokazu Harada, Otawara (JP); Satoshi Ota, Nikko (JP); Makoto Nakano, Nasushiobara (JP); Yasutaka Shindo, Nasushiobara (JP); Katsumi Gotanda, Nasushiobara (JP)

(73) Assignees: Kabushiki Kaisha Toshiba, Tokyo (JP); Toshiba Medical Systems Corporation, Tochigi (JP)

( * ) Notice: Subject to any disclaimer, the term of this patent is extended or adjusted under 35 U.S.C. 154(b) by 97 days.

(21) Appl. No.: 12/433,151

(22) Filed: Apr. 30, 2009

(65) Prior Publication Data

US 2009/0279660 A1 Nov. 12, 2009

(30) Foreign Application Priority Data

May 9, 2008 (JP) ............................. 2008-123935

(51) Int. Cl.
*H05G 1/60* (2006.01)
*H01J 35/10* (2006.01)

(52) U.S. Cl. ........................................ 378/19; 378/199
(58) Field of Classification Search ................. 378/4, 378/15, 19, 130, 199, 200

See application file for complete search history.

(56) References Cited

U.S. PATENT DOCUMENTS

| 4,115,697 | A | * | 9/1978 | Hounsfield et al. | ............ 378/15 |
| 4,831,639 | A | * | 5/1989 | Harke | ............ 378/19 |
| 5,660,917 | A | | 8/1997 | Fujimori et al. | ............ 428/195 |
| 6,491,428 | B1 | * | 12/2002 | Takanashi | ............ 378/200 |
| 6,709,156 | B1 | * | 3/2004 | Hell et al. | ............ 378/199 |
| 7,215,740 | B2 | | 5/2007 | Fukushima et al. | ............ 378/126 |
| 7,311,439 | B2 | * | 12/2007 | Muller | ............ 378/199 |
| 7,324,629 | B2 | | 1/2008 | Fukushima et al. | ............ 378/126 |
| 7,697,665 | B2 | | 4/2010 | Yonezawa et al. | ............ 378/130 |
| 7,746,982 | B2 | | 6/2010 | Yoshii et al. | ............ 378/133 |
| 2009/0041181 | A1 | * | 2/2009 | Krug | ............ 378/19 |
| 2009/0080616 | A1 | | 3/2009 | Yoshii et al. | ............ 378/133 |

(Continued)

FOREIGN PATENT DOCUMENTS

JP 10234721 A 9/1998

(Continued)

OTHER PUBLICATIONS

U.S. Appl. No. 12/408,514, filed Mar. 20, 2009.

(Continued)

*Primary Examiner*—Irakli Kiknadze
(74) *Attorney, Agent, or Firm*—Ohlandt, Greeley, Ruggiero & Perle, L.L.P.

(57) ABSTRACT

A rotor is rotatably supported in a gantry housing having a substantially sealed structure. An X-ray tube is provided in the rotor. A cooler is provided in the rotor and cools a refrigerant within the X-ray tube. An X-ray detector is provided in the rotor. A reconstruction unit reconstructs an image on the basis of an output of the X-ray detector. A radiator is fixed inside the gantry housing at a position opposite to an exhaust opening of the cooler when the rotor is stationary.

14 Claims, 9 Drawing Sheets

U.S. PATENT DOCUMENTS

2009/0225950 A1 9/2009 Yonezawa et al. ............ 378/133
2009/0245469 A1 10/2009 Ito et al. ..................... 378/133

FOREIGN PATENT DOCUMENTS

JP 2003144425 A 5/2003

OTHER PUBLICATIONS

U.S. Appl. No. 12/211,721, filed Sep. 16, 2008.
U.S. Appl. No. 12/469,254, filed May 20, 2009, Yonezawa.

* cited by examiner

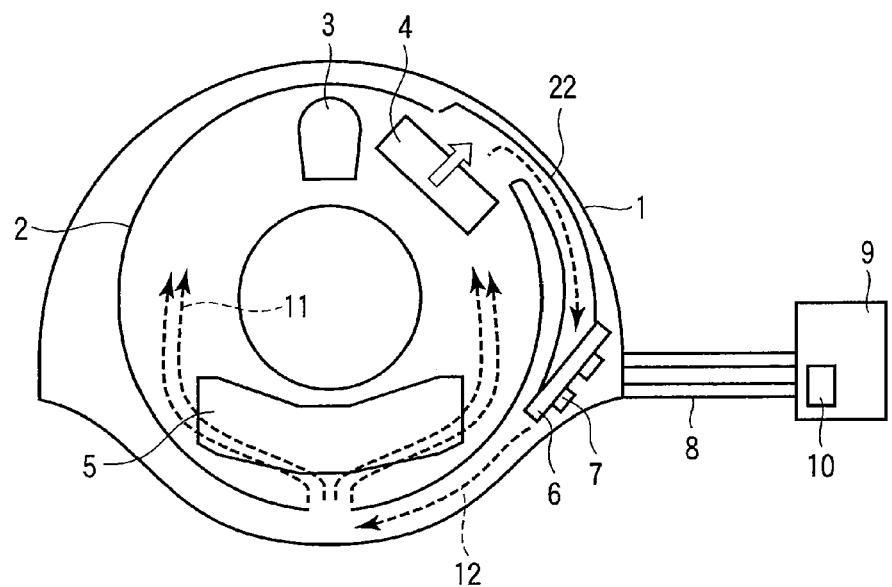
F I G. 10
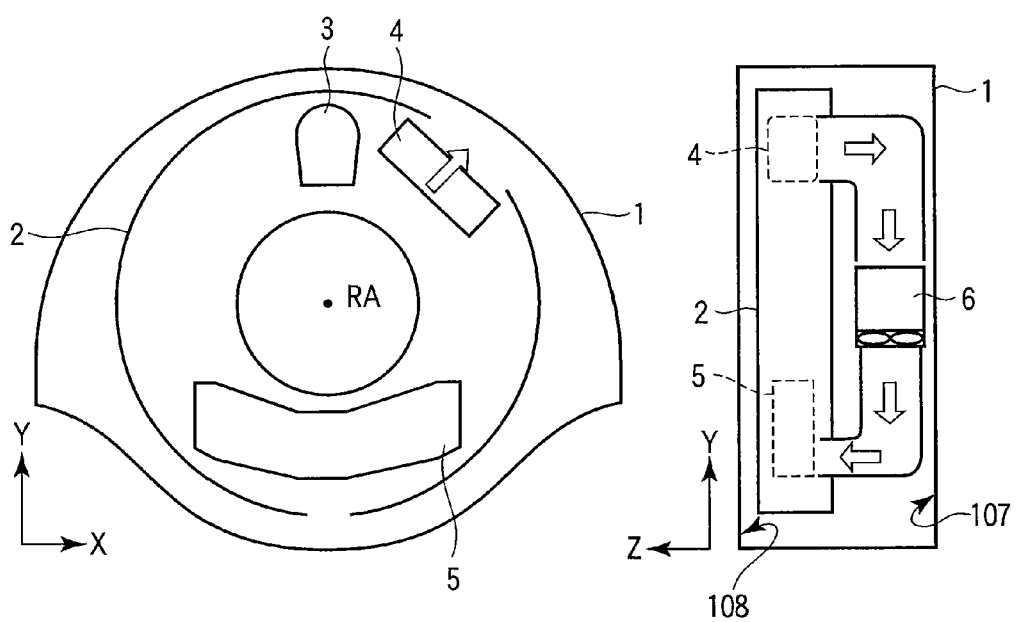
F I G. 11A   F I G. 11B

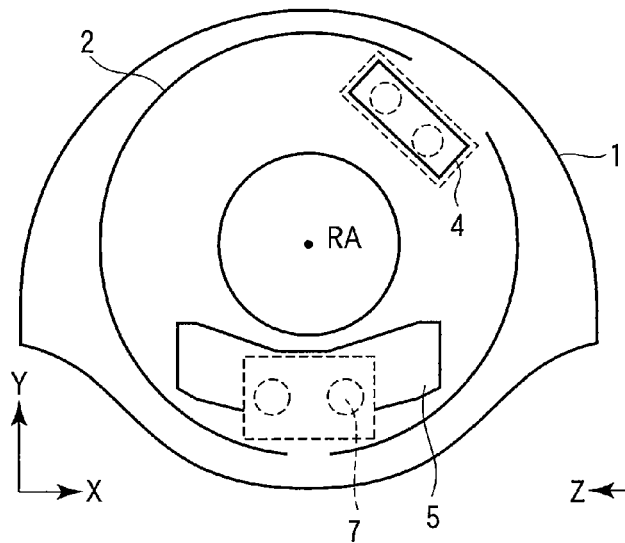
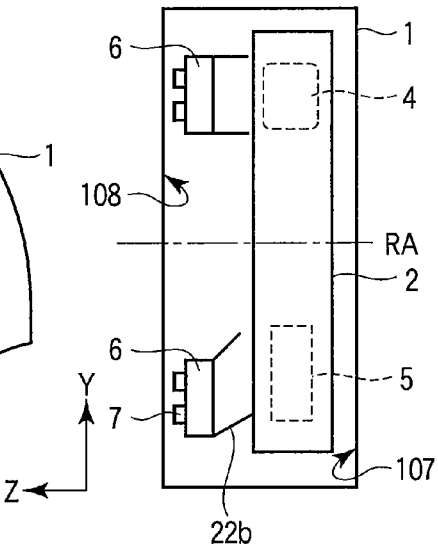
FIG. 12A  FIG. 12B
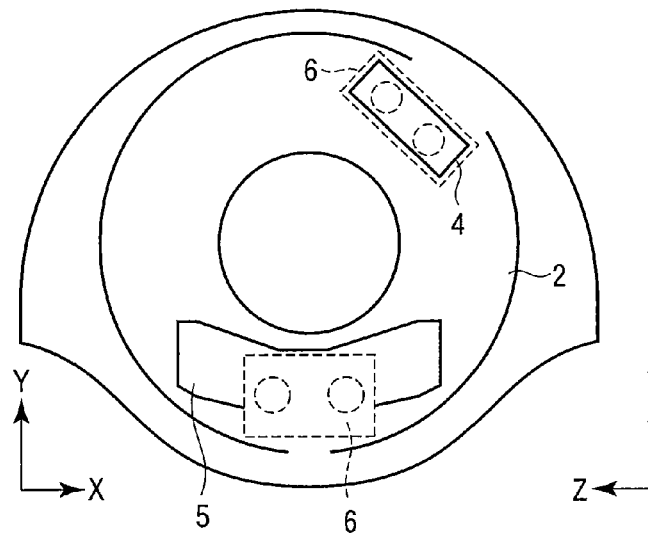
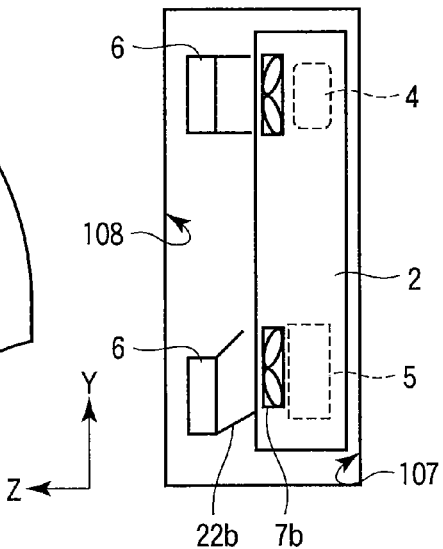
FIG. 13A  FIG. 13B 18b · · · Duct is bent in rotor direction to efficiently send air into rotor
18c · · · Duct is diffuser-shaped to send air over wide range
18d · · · Duct is nozzle-shaped to accelerate air and ensure that air is sent into rotor even when distance between duct outlet and rotor is great

X-RAY COMPUTED TOMOGRAPHIC APPARATUS

CROSS-REFERENCE TO RELATED APPLICATIONS

This application is based upon and claims the benefit of priority from prior Japanese Patent Application No. 2008-123935, filed May 9, 2008, the entire contents of which are incorporated herein by reference.

BACKGROUND OF THE INVENTION

1. Field of the Invention

The present invention relates to cooling the inside of a gantry having an X-ray tube and an X-ray detector in an X-ray computed tomographic apparatus (computer tomography (CT)).

2. Description of the Related Art

JP-A 2003-144425 proposes a method wherein elements in a rotor are partitioned by walls to separately control the atmospheric temperatures in the respective elements. However, a gantry housing is not substantially sealed off from the outside, and is not structured to be able to inhibit noise or exhaust heat into an examination room. This document describes in FIG. 4 the provision of an heat exchanger within the gantry housing, but does not describe any structure for obtaining an efficient cooling function.

JP-A 10-234721 proposes the structure of a gantry housing designed to prevent dust which may lead to decreased performance or a breakdown from being accumulated in a gantry. This structure has a double cover, but is not designed to guide the air in a gantry to another place, so that the gantry housing is not substantially sealed off from the outside.

An X-ray computed tomographic apparatus is capable of displaying, substantially in real time, tomograms or three-dimensional images of organs in a patient that are invisible to the naked eye. Such an X-ray computed tomographic apparatus is currently an essential medical instrument in the most advanced medical field where rapid and proper medical practices are needed. In order to meet the high clinical needs, further technological enhancement is being made, but, on the other hand, problems are occurring, such as noise produced by exhaust air from fans or heat released into the examination room. That is, if noise increases along with an increase in the amount of air from the exhaust fan for letting out a great amount of heat generated in the gantry, not only a conversation between a patient and a doctor may be prevented but also the patient may feel uneasy. Moreover, the amount of exhaust heat from an X-ray tube is already so great as to impose a high load on the air-conditioning equipment in the examination room. More exhaust heat restricts the place where the apparatus can be installed.

However, as the X-ray computed tomographic apparatus uses a technique for forming an image from X-ray detector signals obtained at a plurality of angles, the X-ray tube that generates a great amount of heat has to be installed inside the rotor. It is thus difficult to directly cool the X-ray tube alone. Therefore, according to a method generally used, exhaust heat from an X-ray tube cooler installed in the rotor is once released into a space between the rotor and the gantry housing, and then discharged to the examination room by the exhaust fan attached to the gantry housing. It is however difficult to inhibit the noise or the heat release into the examination room as long as the structure remains the same.

BRIEF SUMMARY OF THE INVENTION

According to an aspect of the present invention, there is provided an X-ray computed tomographic apparatus comprising: a rotor rotatably supported in a gantry housing having a substantially sealed structure; an X-ray tube provided in the rotor; a cooler which is provided in the rotor and which cools a refrigerant within the X-ray tube; an X-ray detector which is provided in the rotor and which detects X-rays transmitted through a subject; a reconstruction unit which reconstructs an image on the basis of an output of the X-ray detector; and a radiator which is fixed inside the gantry housing at a position opposite to an exhaust opening of the cooler when the rotor is stationary.

BRIEF DESCRIPTION OF THE SEVERAL VIEWS OF THE DRAWING

FIG. 10 is a schematic diagram for another modification of the present embodiment;

FIGS. 11A and 11B are schematic diagrams for another modification of the present embodiment;

FIGS. 12A and 12B are schematic diagrams for another modification of the present embodiment;

FIGS. 13A and 13B are schematic diagrams for another modification of the present embodiment;

DETAILED DESCRIPTION OF THE INVENTION

An embodiment of the present invention will hereinafter be described with reference to the drawings. First, the basic configuration of an X-ray computed tomographic apparatus is explained.

Figure 1:
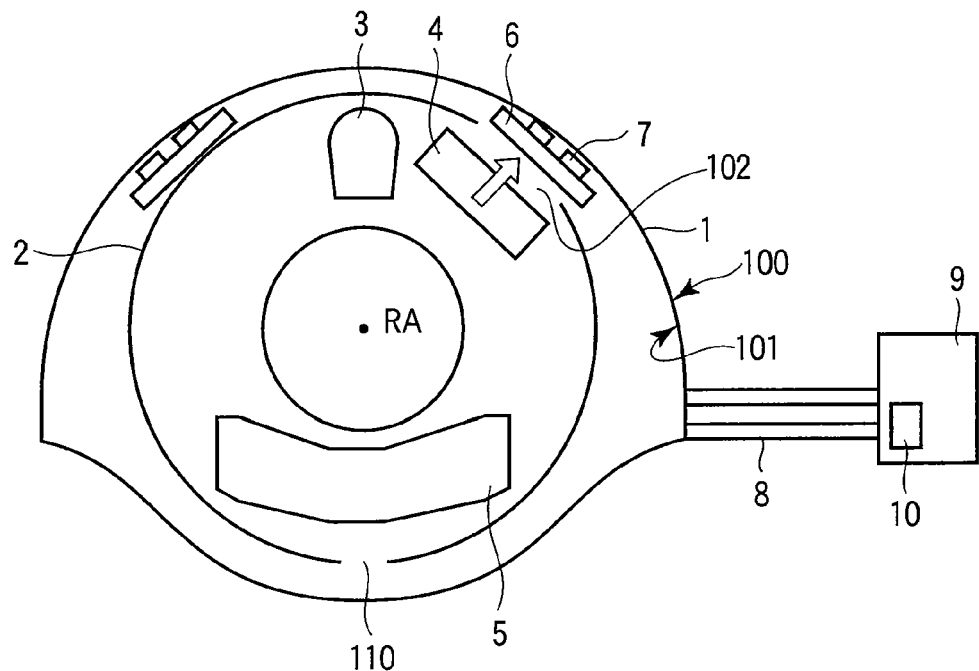
FIG. 1 is a diagram showing a structure inside a gantry according to an embodiment.

FIG. 1 shows the internal structure of a gantry of the X-ray computed tomographic apparatus according to the present embodiment, wherein a front cover of a gantry housing is removed. A gantry 100 has an X-ray tube 3 for generating X-rays. A tube voltage is applied and a filament current is supplied to the X-ray tube 3 from a high voltage generator via a slip ring mechanism, such that the X-ray tube 3 generates X-rays. The X-ray tube 3 is installed together with an X-ray detector 5 in a rotor 2 which is supported rotatably around a rotation axis RA. A gantry rotating unit is provided to rotate the rotor 2. The X-ray detector 5 faces the X-ray tube 3 across the rotation axis RA. An cylindrical imaging region is provided around the rotation axis RA, and a subject is placed in the imaging region. The X-ray detector 5 detects the X-rays transmitted through the subject from the X-ray tube 3. The X-ray detector 5 is a multi-slice type or two-dimensional array type X-ray detector. That is, the X-ray detector 5 has a plurality of X-ray detection element arrays arranged along the rotation axis RA. Each of the X-ray detection element arrays has a plurality of X-ray detection elements aligned along a direction perpendicular to the rotation axis RA.

An output of the X-ray detector 5 is amplified for each channel by a data acquisition circuit (DAS), converted to a digital signal, and sent to a preprocessor via, for example, a contactless data transfer unit where the digital signal is subjected to a correction such as a sensitivity correction. Then, the corrected signal is stored in a projection data storage as so-called projection data present at a stage immediately before reconstruction. A scan controller controls the gantry rotating unit, the high voltage generator, the data acquisition circuit, etc. for the purpose of data acquisition (scanning). A reconstruction unit reconstructs tomographic data in accordance with a projection data set which has been acquired during a 360-degree or (180 degrees+fan angle) movement of the X-ray tube 3.

Next, the structure of the gantry 100 is explained. The gantry 100 has a gantry housing 1. The gantry housing 1 has a structure substantially sealed off from the outside. The gantry housing 1 houses the X-ray tube 3, a cooler 4 for cooling the X-ray tube 3, the X-ray detector 5, etc. The cooler 4 is attached to the inside of the substantially cylindrical rotor 2 together with the X-ray tube 3 and the X-ray detector 5. A radiator 6 is fixed to the inner surface of a side cover 101 of the gantry housing 1. The radiator 6 is provided with a fan 7 for forcing air circulation through the radiator 6. Air cooled in the radiator 6 flows along the side cover 101 of the gantry housing 1, and is guided into the rotor 2 through an opening 110 made in the external wall of the substantially cylindrical rotor 2, and then cools the X-ray detector 5 from its rear surface.

The cooler 4 is provided so that the direction of air circulation therein may be coincident with the radial direction of the rotor 2. The radiator 6 is also provided so that the direction of air circulation therein may be coincident with the radial direction of the rotor 2. Here, a rotation system of the rotor 2 is controlled so that the rotor always comes to rest (stops) at a fixed position, typically at a position where the X-ray tube 3 is located at the top. The radiator 6 is provided so that the radiator may be proximate to the cooler 4 through an opening 102 made in the outer periphery of the rotor 2 and may face the cooler 4 in the direction of the air circulation when the rotor 2 is stationary. Thus, the exhaust air from the cooler 4 is directly sucked to the radiator 6.

Figure 2:
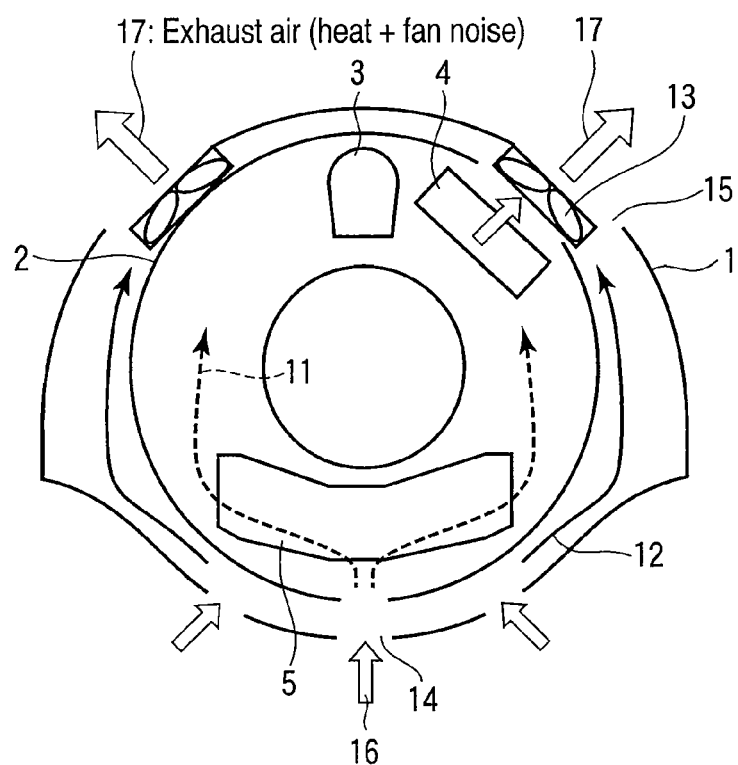
FIG. 2 is a diagram showing the flow of air inside a conventional gantry.

Here, a conventional gantry internal structure is shown in FIG. 2 for comparison. Since an X-ray tube 3 is installed inside a rotor 2, the X-ray tube 3 is once cooled by a cooler 4 which is also installed in the rotor, and then air is discharged from the cooler 4 to the outside of the rotor 2 (to the inside of a gantry housing 1). Subsequently, heat is discharged by an exhaust fan 13 disposed in the gantry housing 1. The flow inside the gantry is as follows: First, there is a suction 16 from an inlet 14 provided in the lower part of the gantry housing 1. Then, there is a circulation 11 around an X-ray detector 5 through the rotor 2 (part of the flow takes a bypass between the rotor 2 and a cover as circulation 12). Subsequently, there is an exhaust 17 by the exhaust fan 13 after discharge from the cooler 4 into a clearance between the rotor 2 and the gantry housing 1. This exhaust 17 entails a great amount of exhaust heat and fan noise.

Figure 3:
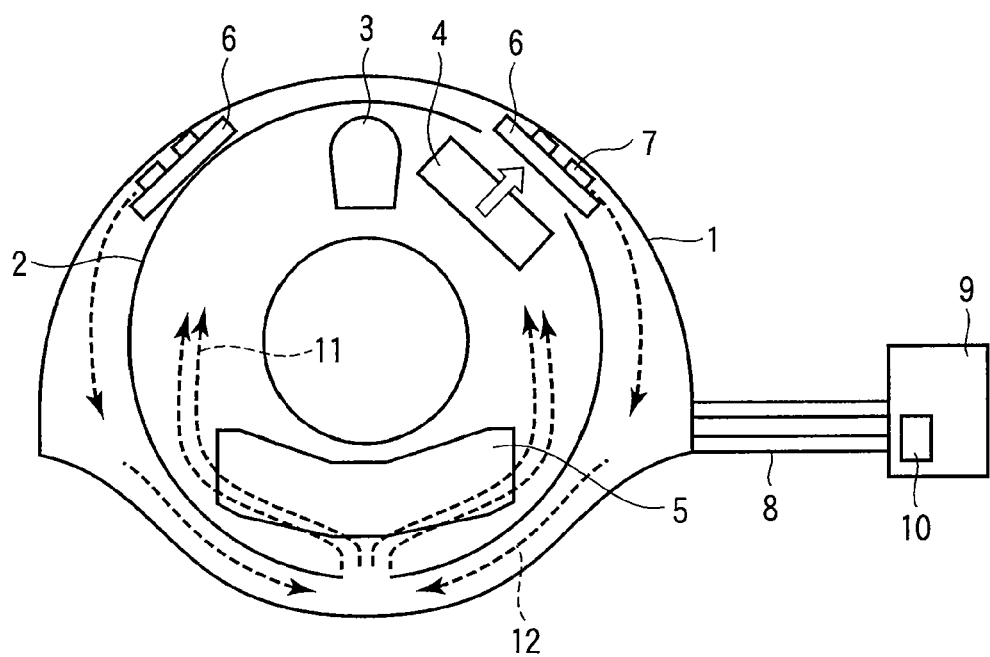
FIG. 3 is a diagram showing the flow of air inside the gantry in the present embodiment.

On the contrary, in the present embodiment, exhaust heat discharged from the cooler 4 as in the conventional type is subjected to a heat exchange by the radiator 6 which is located in proximity to and face to face with the cooler 4 when the rotor is stationary, and cool air thus produced circulates through a clearance between the gantry housing 1 and the rotor 2, as shown in FIG. 3 (see the sign 12). A pipe 8 for circulating a refrigerant, an external temperature controller 9 and a pump 10 are connected to the radiator 6, so that heat in the X-ray tube 3 is let out of the external temperature controller 9. In the present embodiment, no inlet and outlet are needed for the gantry housing 1, and part of the noise of the fan 7 inside can be blocked. If the external temperature controller 9 is moved out of an examination room, exhaust heat into the examination room can be reduced. Moreover, as the gantry is completely sealed up, dust in the examination room is difficult to enter the gantry, which advantageously brings an expected improvement in instrumental reliability.

Figure 4:
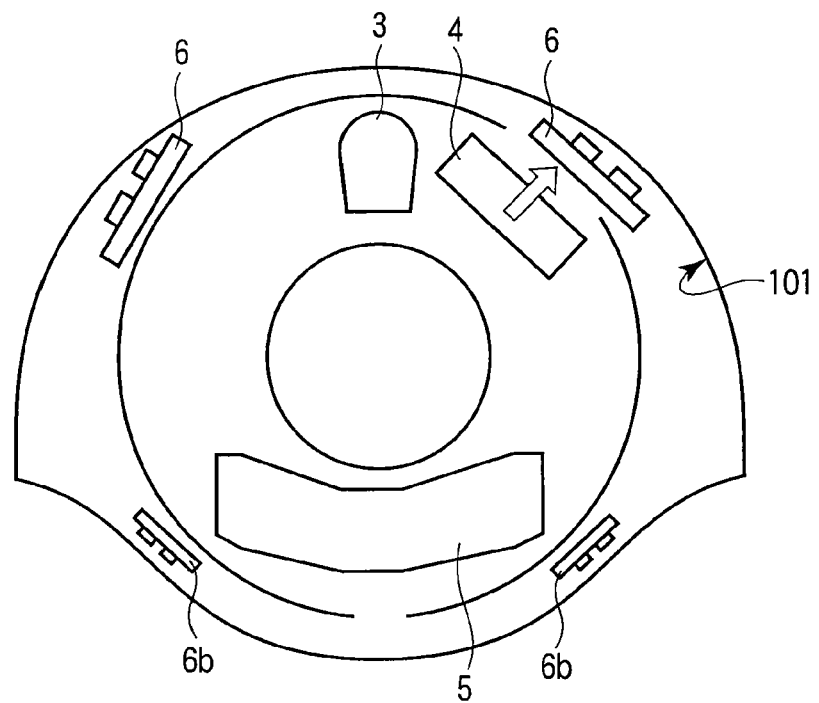
FIG. 4 is a diagram showing the arrangement of a plurality of radiators according to a modification of the present embodiment.

There are two radiators 6 in the example shown in FIG. 3. The number of radiators 6 may be one or may be three or more depending on the cooling performance needed. However, at least one of the radiators 6 is disposed in front of the position at which the oil cooler 4 comes to rest, so that the exhaust air from the cooler 4 at high temperature can be efficiently sent into the radiators 6, and the cooling performance can be enhanced. As shown in FIG. 4, small radiators 6b may be disposed on the inner surface of the side cover 101 of the gantry housing 1 in the vicinity of the X-ray detector 5. Moreover, a blower fan, for example, which can be disposed even in a small space can be used as the fan 7.

Figure 5:
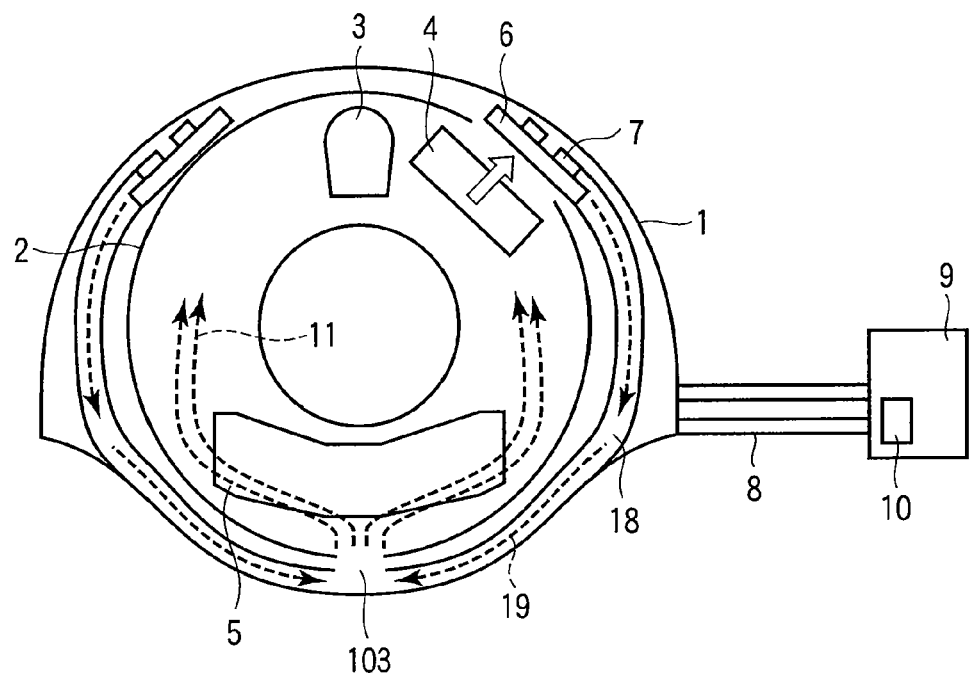
FIG. 5 is a schematic diagram for another modification of the present embodiment.

A modification of the present embodiment is shown in FIG. 5. Cool air after a heat exchange in the radiator 6 is guided to the X-ray detector 5 via an exhaust duct 18 from an opening 103 which is made in the outer periphery of the rotor 2 substantially in the vicinity of the center of the X-ray detector 5. Then, the cool air cools the X-ray detector 5. In this case, the exhaust duct 18 preferably extends along the inner wall of the side cover 101 of the gantry housing 1 so that the rotation of the rotor 2 may not be prevented. The duct 18 is typically formed of a pipe. The inner wall of the side cover 101 may be used as part of the duct 18.

Figure 17:
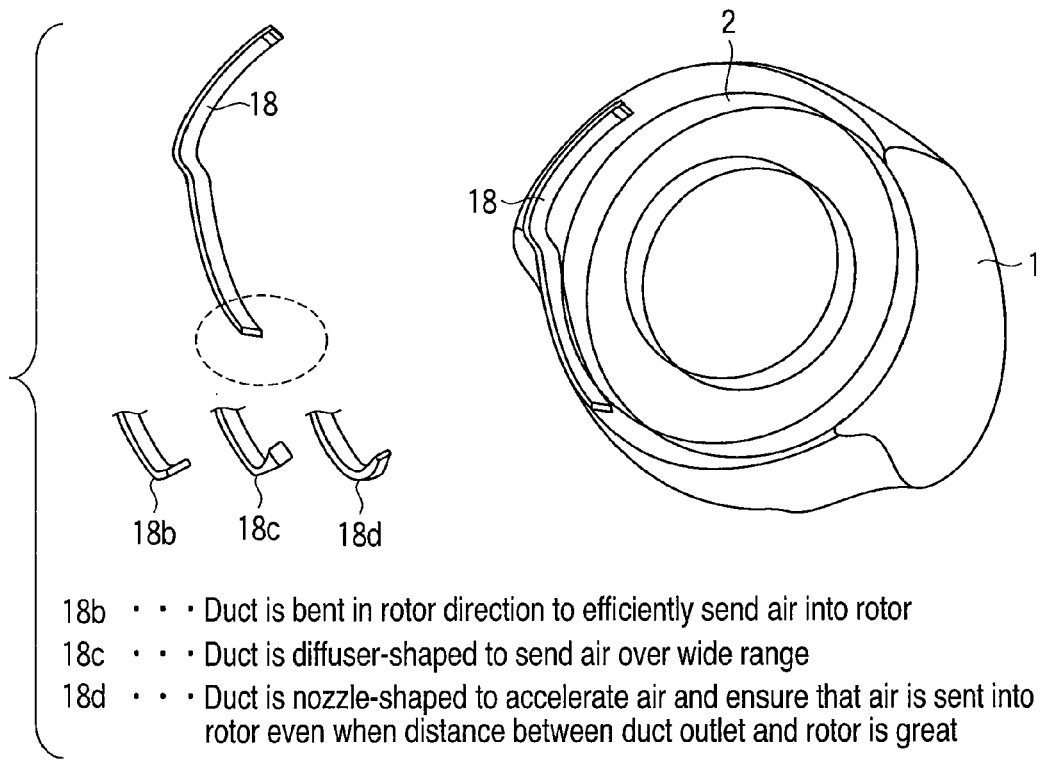
FIG. 17 is a schematic diagram for another modification of the present embodiment.

In addition, the shape of the tip of the exhaust duct 18 can be changed to enhance the cooling effect of the X-ray detector 5. For example, as shown in FIG. 17, the tip of an exhaust duct 18b is bent toward the rotor 2 to efficiently send air into the rotor 2. Alternatively, the tip of an exhaust duct 18c may be bent toward the rotor 2, and its nozzle may be conically shaped to improve the diffuser effect (diffusing effect) of the cool air. Alternatively, the tip of an exhaust duct 18d may be bent toward the rotor 2, and its nozzle may be sharply shaped to accelerate the cool air, thereby improving the accuracy of sending air into the rotor 2.

Figure 6:
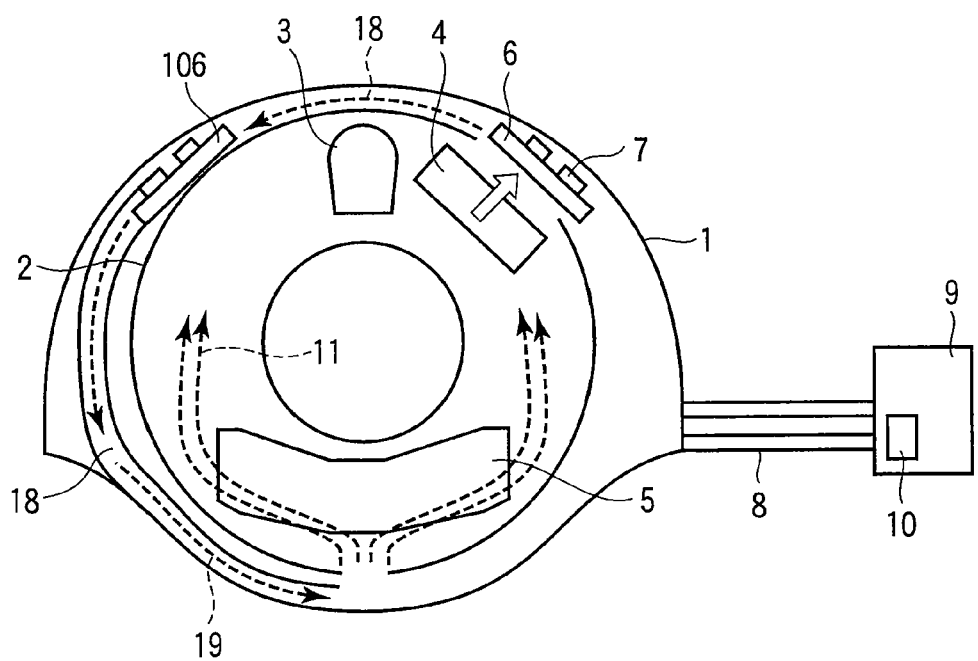
FIG. 6 is a schematic diagram for another modification of the present embodiment.

Owing to the structure of the duct 18, there is no effect of changes in air flow dependent on whether the rotor 2 is rotating. This allows simplification in the design for cooling and makes it possible to inhibit the increase of noise due to interference between air flow of the rotation and air flow of the fan 7. Another modification is shown in FIG. 6. A plurality of radiators 6 are disposed. For example, when the air which has not been cooled by the first radiator is to be cooled by a second radiator 106, the radiators 6, 106 may be connected to each other by the duct 18. Although the duct 18 is located on the side surface of the rotor 2 in the illustrations in FIGS. 5 and 6, the duct 18 may be in such a form as to cling to the rear side of the rotor 2 or to the front cover.

Figure 7:
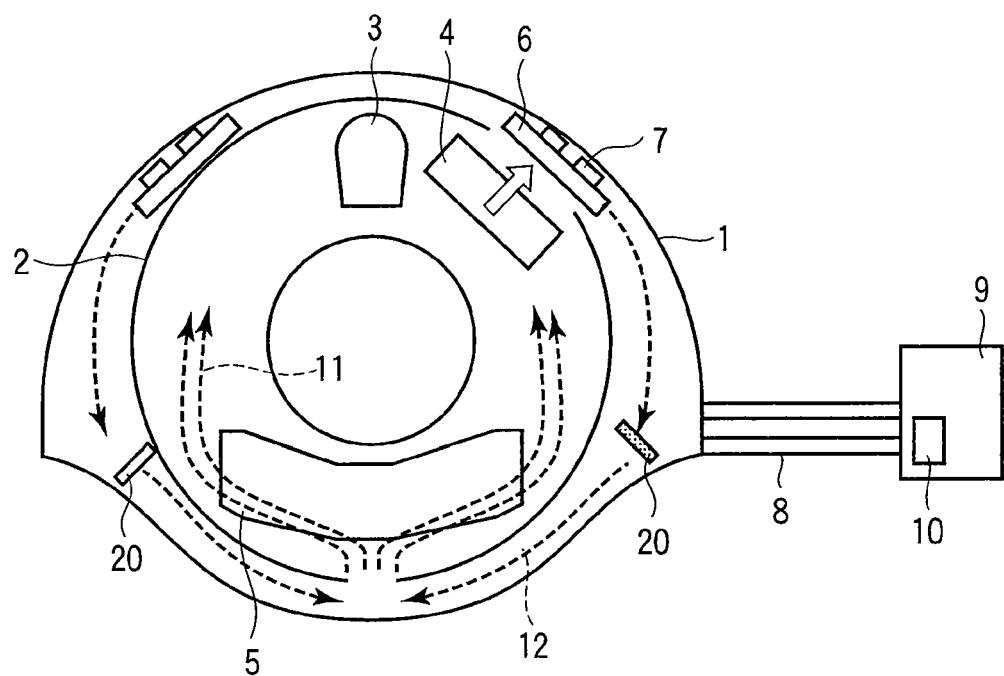
FIG. 7 is a schematic diagram for another modification of the present embodiment.
Figure 8:
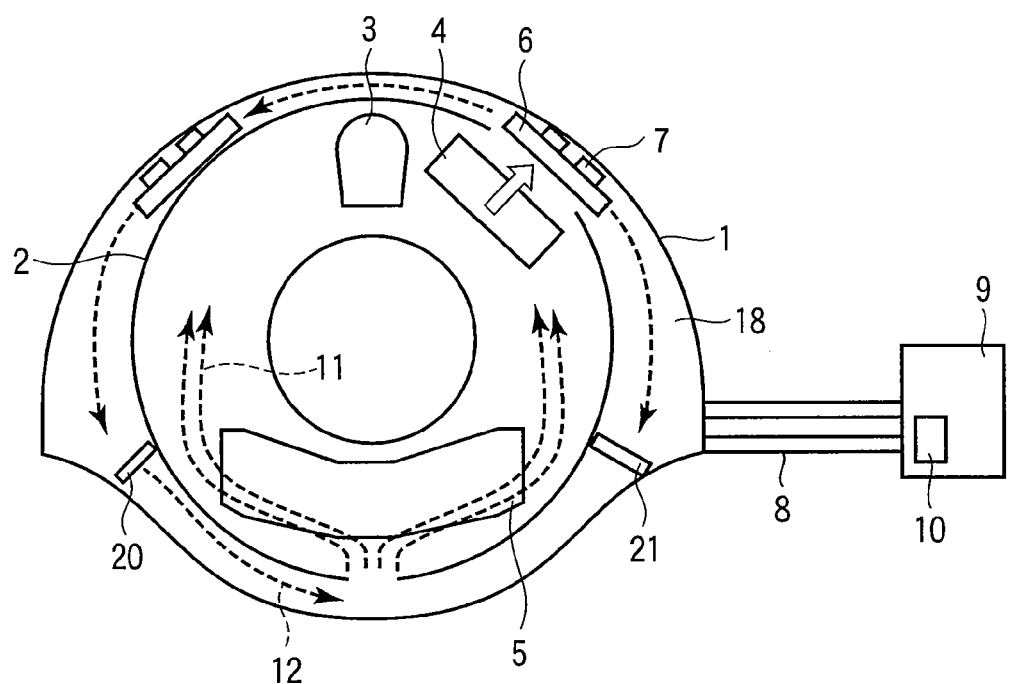
FIG. 8 is a schematic diagram for another modification of the present embodiment.
Figure 9:
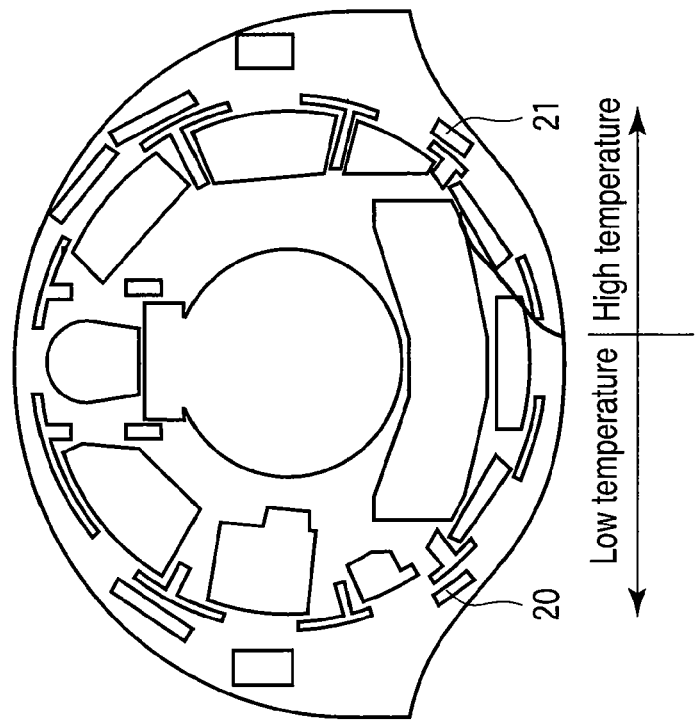
FIG. 9 is a diagram showing numerical analytic results indicating the effects of another modification of the present embodiment.
Figure 9:
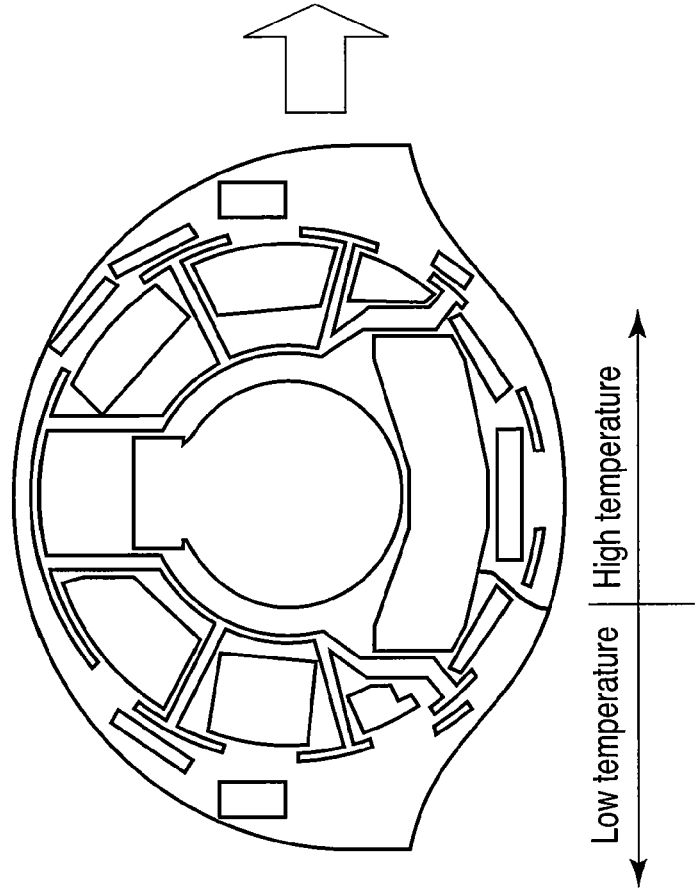

Another modification is shown in FIG. 7. When a clearance between the gantry housing 1 and the rotor 2 is narrow or when an exhaust duct is difficult to place, an assist fan 20 is used to force cool air to circulate in the gantry housing 1 so that the cool air after a heat exchange in the radiator 6 can be sent to, for example, the X-ray detector 5. Still another modification is shown in FIG. 8. A partition plate 21 is disposed in the duct 18 together with an assist fan 20. Thus, cool air from the radiator 6 can be effectively brought to any place. The effects of the assist fan 20 and the partition plate 21 found out by a numerical analysis are shown in FIG. 9. In addition, the assist fan 20 may be stopped or a movable portion may be provided to move the assist fan 20 and the partition plate 21 so that the assist fan 20 and the partition plate 21 do not prevent the rotation of the rotor 2.

Another modification is shown in FIG. 10. When a radiator 6 can not be disposed directly opposite to a cooler 4 due to designed instrumental layout, the radiator 6 is disposed face to face with the cooler 4 via an exhaust duct 22, so that high-temperature air from the cooler 4 can be sent to the radiator 6 disposed at any place, and cooling performance is easily ensured.

Another modification is shown in FIGS. 11A and 11B and FIGS. 12A and 12B. The radiator 6 may be disposed in the housing 1 in a space between the rotor 2 and a back cover 107 (or a front cover 108) of the housing 1. In FIG. 12, in the space between the rotor 2 and the front cover 108 of the housing 1, the radiators 6 are installed at a position in front of the X-ray detector 5 and at a position in front of the X-ray tube 3 when the rotor 2 is stationary. A duct 22b which connects the X-ray detector 5 and the radiator 6 allows exhaust air to be efficiently passed to the radiator 6. In this case, the radiators 6 are placed so that the directions of flows therein may be substantially parallel to the rotation axis RA of the rotor 2.

Another modification is shown in FIGS. 13A and 13B. The fan 7 is combined with the radiator in FIG. 12. In contrast, in the example shown in FIGS. 13A and 13B, air is sent into the radiator 6 by directly sucking exhaust air from a fan which is originally provided in the rotor 2. It goes without saying that the X-ray detector exhaust duct 22b may be provided.

Figure 14:
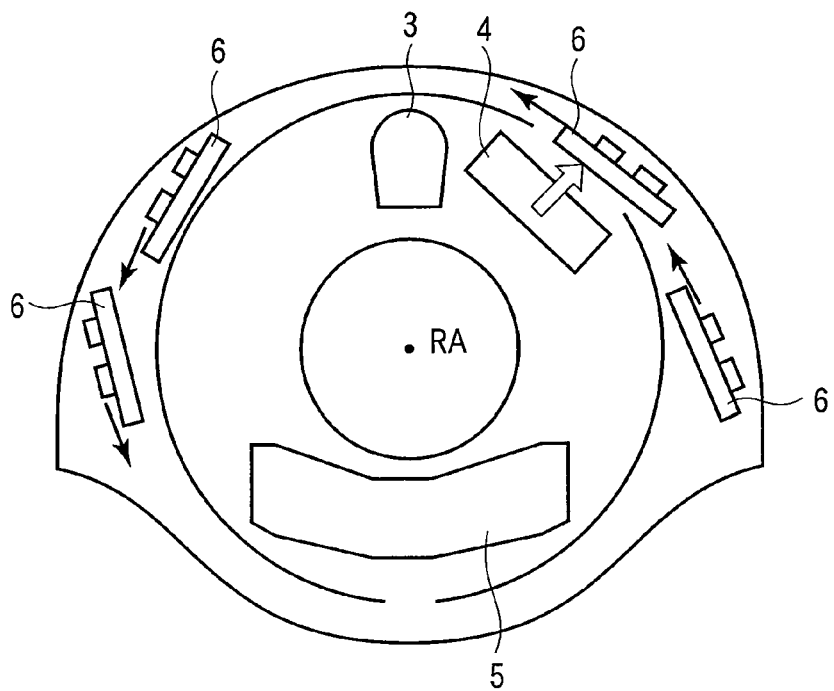
FIG. 14 is a schematic diagram for another modification of the present embodiment.

As shown in FIG. 14, the directions of flows in the plurality of radiators 6 arranged are not parallel to the radial direction of the rotor 2 but inclined. The angle of inclination is different in each of the radiators 6. These angles of inclination are adjusted with respect to each other so that exhaust air from one radiator 6 may be sucked into another adjacent radiator 6. Consequently, exhaust air can be efficiently sent to the adjacent radiator 6 without particularly using any duct, and cooling performance can be improved.

Figure 15:
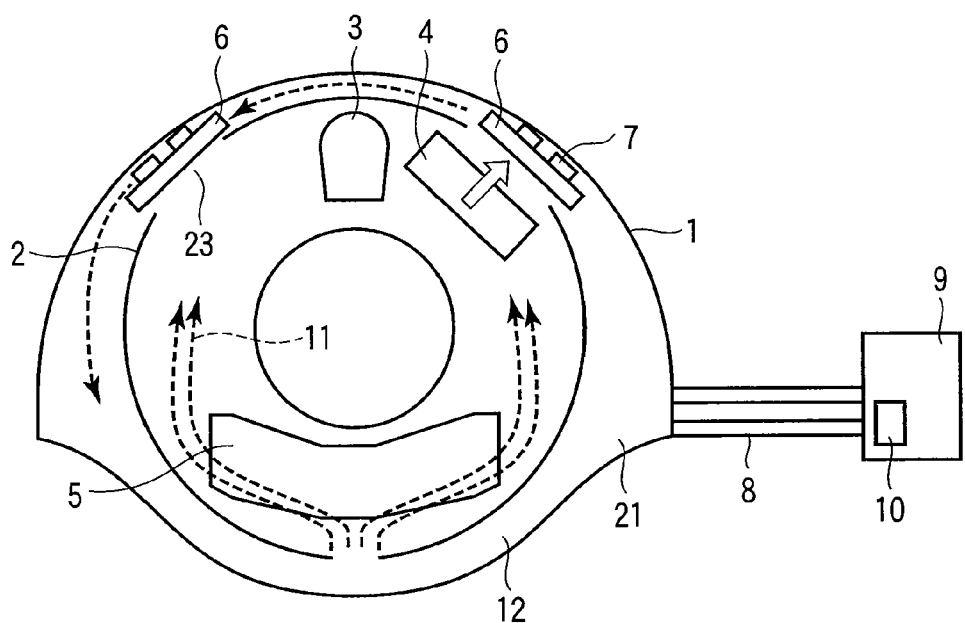
FIG. 15 is a schematic diagram for another modification of the present embodiment.

Another modification is shown in FIG. 15. When a plurality of radiators 6 are installed, openings (ventilation holes) 23 are provided in the outer peripheral surface of the rotor 2 corresponding to the positions of the radiators 6. This makes it easier for the radiator 6 which is not located in front of the cooler 4 to perform the heat exchange of the air warmed in the rotor 2, thereby enabling an improvement in the cooling performance.

Furthermore, when the rotor 2 is cylindrical (drum-shaped), its outer peripheral part is typically connected to its inner peripheral part by ribs to increase rigidity. If holes are made at the roots (close to the centers in a depth direction) of the ribs, the holes can be made to locate the ventilation holes 23 without decreasing the strength of the rotor 2. Moreover, the holes are not easily closed even after installation of the apparatus within the rotor, so that the air inside the rotor 2 can be efficiently sent to the outside of the rotor 2.

Figures 16A, 16B:
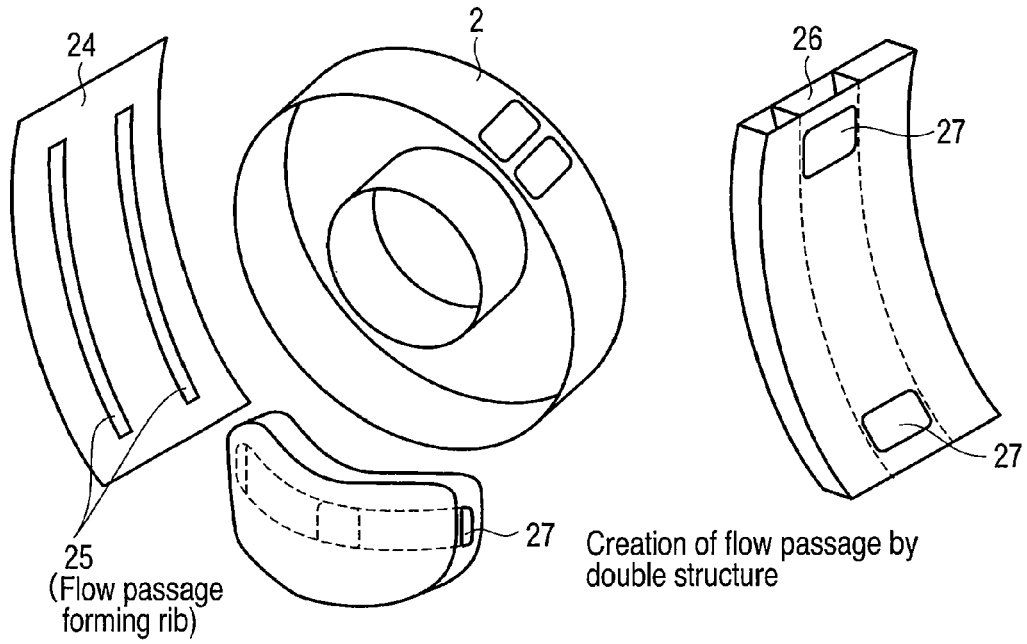
FIGS. 16A and 16B are schematic diagrams for another modification of the present embodiment.

Another modification is shown in FIGS. 16A and 16B. A cylindrical member is newly installed as the exhaust duct for sending cool air from the radiator 6 to another place. Moreover, as shown in shown in FIG. 16A, ribs 25 are attached to a side cover 24 along its circumferential direction. As a result, a duct structure is formed. Alternatively, a duct structure can also be formed by providing ventilation ducts 27 in a double cover 26, 26b.

According to the embodiment described above, the noise of the exhaust fan can be considerably reduced in the X-ray computed tomographic apparatus, which not only allows smoother communication between a patient and a doctor but also removes the patient of uneasiness triggered by the noise. Further, since exhaust heat can be let out of the examination room by the external temperature controller, air-conditioning equipment to be required for the examination room is minimized, and places to install the apparatus can be significantly increased. Moreover, as the gantry housing has a substantially sealed structure, dust in the examination room can be inhibited from entering the gantry, and the apparatus can be increased in reliability.

In addition, according to this embodiment, efficient cooling can be performed around an X-ray detector DAS, and the temperature around the X-ray detector DAS can be reduced. This makes it possible to acquire an X-ray tomogram having less noise in the case of low-dose tomography. Moreover, changes in the temperature around the X-ray detector can be inhibited, and variations in detection efficiency due to the temperature changes can therefore be reduced. That is to say, creation of abnormal images depending on the temperature changes can be inhibited.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
   a rotor rotatably supported in a gantry housing having a substantially sealed structure;
   an X-ray tube provided in the rotor;
   a refrigerant and a cooler which are provided in the rotor and which cool the X-ray tube;
   an X-ray detector which is provided in the rotor and which detects X-rays transmitted through a subject;
   a reconstruction unit which reconstructs an image on the basis of an output of the X-ray detector; and
   a radiator which is fixed inside the gantry housing at a position opposite to an exhaust opening of the cooler when the rotor is stationary.

2. The apparatus of claim 1, wherein an air passage is formed inside the gantry housing to bring cool air generated by a heat exchange in the radiator to the vicinity of the X-ray detector when the rotor is stationary.

3. The apparatus of claim 1, wherein the air passage is a duct.

4. The apparatus of claim 1, wherein an inner wall of the gantry housing is used as part of the air passage.

5. The apparatus of claim 1, wherein an assist fan is provided inside the gantry housing to send cool air generated by a heat exchange in the radiator to the vicinity of the X-ray detector when the rotor is stationary.

6. The apparatus of claim 1, wherein a fan is disposed in the vicinity of the radiator to compulsorily circulate air through the radiator.

7. The apparatus of claim 1, further comprising a sub-radiator which is fixed inside the gantry housing in the vicinity of the X-ray detector when the rotor is stationary.

8. The apparatus of claim 7, further comprising a fan to compulsorily pass air to the sub-radiator.

9. The apparatus of claim 7, wherein the sub-radiator is disposed on a side cover of the gantry housing.

10. The apparatus of claim 7, wherein the sub-radiator is disposed on a front cover of the gantry housing.

11. The apparatus of claim 1, wherein a plurality of radiators are provided, the plurality of radiators being arranged so that the directions of air flows therein are different from each other.

12. The apparatus of claim 1, wherein a plurality of radiators are provided, the plurality of radiators being arranged so that air flow passages therein are substantially connected to each other.

13. The apparatus of claim 1, wherein a side cover of the gantry housing is provided with a guide structure which guides the flow of cool air discharged from the radiator.

14. An X-ray computed tomographic apparatus comprising:
- a rotor rotatably supported in a gantry housing having a substantially sealed structure;
- an X-ray tube provided in the rotor;
- a cooler which is provided in the rotor and which cools a refrigerant within the X-ray tube;
- an X-ray detector which is provided in the rotor and which detects X-rays transmitted through a subject;
- a reconstruction unit which reconstructs an image on the basis of an output of the X-ray detector; and
- a radiator which is fixed inside the gantry housing at a position where this radiator is connected to an exhaust opening of the cooler via a duct when the rotor is stationary.

* * * * *